United States Patent [19]

Yue

[11] Patent Number: 6,048,544
[45] Date of Patent: Apr. 11, 2000

[54] METHOD OF COLLAGEN THERAPY USING RELAXIN

[76] Inventor: Samuel K. Yue, 4928 Hoppy La., Edina, Minn. 55435

[21] Appl. No.: 09/196,292

[22] Filed: Nov. 19, 1998

Related U.S. Application Data

[62] Division of application No. 09/005,383, Jan. 9, 1998, Pat. No. 5,863,552, which is a division of application No. 08/802,340, Feb. 11, 1997, Pat. No. 5,707,642, which is a continuation of application No. 08/560,492, Nov. 17, 1995, Pat. No. 5,612,051.

[51] Int. Cl.$^7$ ...................................................... A61F 13/02
[52] U.S. Cl. .............................................................. 424/443
[58] Field of Search ............................................. 424/443

[56] References Cited

U.S. PATENT DOCUMENTS

| | | |
|---|---|---|
| 4,267,101 | 5/1981 | Bigazzi . |
| 4,624,804 | 11/1986 | Voelter et al. . |
| 4,656,249 | 4/1987 | Tregear et al. . |
| 4,835,251 | 5/1989 | Burnier et al. . |
| 5,089,419 | 2/1992 | Kuniyuki . |
| 5,108,897 | 4/1992 | Steinetz et al. . |
| 5,145,962 | 9/1992 | Hudson et al. . |
| 5,166,191 | 11/1992 | Cronin et al. . |
| 5,179,195 | 1/1993 | Hudson et al. . |
| 5,223,408 | 6/1993 | Goeddel et al. . |
| 5,279,942 | 1/1994 | Kuniyuki . |
| 5,320,953 | 6/1994 | Hudson et al. . |
| 5,326,694 | 7/1994 | Hudson et al. . |
| 5,451,572 | 9/1995 | Cipolla et al. . |
| 5,464,756 | 11/1995 | Henner et al. . |
| 5,478,807 | 12/1995 | Cronin et al. . |
| 5,656,592 | 8/1997 | Seed et al. . |
| 5,753,623 | 5/1998 | Amento et al. . |
| 5,759,807 | 6/1998 | Breece et al. . |
| 5,811,388 | 9/1998 | Friend et al. . |
| 5,811,395 | 9/1998 | Schwabe et al. . |

OTHER PUBLICATIONS

Gerson Weiss et al., "Elevated First–Trimester Serum Relaxin Concentrations in Pregnant Women Following Ovarian Stimulation Predict Prematurity Risk and Preterm Delivery", Obstetrics & Gynecology, vol. 82, No. 5, Nov. 1993, pp. 821–828.

R.J. Winn et al., "Hormonal Control of the Cervix in Pregnant Gilts. IV. Relaxin Promotes Changes in the Histological Characteristics of the Cervix That Are Associated with Cervical Softening During Late Pregnancy in Gilts", Endocrinology, vol. 133, No. 1, 1993, pp. 121–128.

Erika Bullesbach et al., "Functional Importance of the A Chain Loop in Relaxin and Insulin", The Journal of Biological Chemistry, vol. 269, No. 18, Issue of May 6, pp. 13124–13128, 1994.

Critchley et al., "Is ovarian Relaxin a Stimulus to Placental Protein 14 Secretion in Pregnancy?", Journal of Endocrinology, 1994, vol. 142, pp. 375–378.

Jose M. Colon et al., "Relaxin Secretion into Human Semen is Independent of Gonadotropin Stimulation", Biology of Reprodoction, vol. 50, pp. 187–192, 1994.

B.A. Evans et al., "Characterization of Two RElaxin Genes in the Chimpanzee", Journal of Endocrinology, 1994, vol. 140, pp. 385–392.

Mari S. Golub et al., "Effect of Short–Term Infusion of Recombinant Human Relaxin on Blood Pressure in the Late–Pregnant Rhesus Macaque (Macaca mulatta)", Obstetrics & Gynecology, vol. 83, No. 1, Jan. 1994, pp. 85–88.

Eric Jauniaux et al., "The Role of Relaxin in the Development of the Uteroplacental Circulation in Early Pregnancy", Obstetrics & Gynecology, pp. 338–342 (missing pp. 339 and 341).

M.R. Johnson et al., "The Regulation of Plasma Relaxin Levels During Human Pregnancy", Journal of Endocrinology, 1994, vol. 142. pp. 261–265.

Bernard Lane et al., "Decidualization of Human Endometrial Stromal Cells In Vitro: Effects of Progestine and Relaxin on the Ultrastructure and production of decidual Secretory Proteins", Human Reproduction, vol. 9, No. 2. pp. 259–266, 1994.

Francesco Lanzafame et al.. "Pharmacological Stimulation of Sperm Motility". Human Reproduction. vol. 9. No. 2. pp. 192–199, 1994.

Lone Kjeld Petersen et al., "Normal Serum RElaxin in Women with Disabling Pelvic Pain During Pregnancy". Gynecol Obstet Invest. 1994. vol. 38, pp. 21–23.

G.N. Stemmermann et al., "Immunocytochemical Identification of a Relaxin–Like Protein in Gastrointestinal Epithelium and Carcinoma: A Preliminary Report", Journal of Endocrinology, 1994, vol. 140, pp. 321–325.

L.S. Tashima et al., "Human Relaxins in Normal, Benign and Neoplastic Breast Tissue", Journal of Molecular Endocrinology, 1994, vol. 12, pp. 351–364.

R.J. Winn et al., "Individual and Combined Effects of Relaxin, Estrogen, and Progesterone in Ovariectomized Gilts. I. Effects on the Growth, Softening, and Histological Properties of the Cervix", Endocrinology, 1994, vol. 135. No. 3, pp. 1241–1249.

Seth Guller et al., "Negative Regulation of Placental Fibronectin Expression by Glucocorticoids and Cyclic Adenosine3',5'–Monophosphate$^{a,b}$", Annals New York Academy of Sciences, pp. 132–142, Sep. 1994.

Alastair H. MacLennan et al., "Ripening of the Human Cervix and Induction of Labor with Intracervical Purified Porcine Relaxin", Obstetrics & Gynecology, vol. 68, No. 5, Nov. 1986, pp. 598–601.

(List continued on next page.)

*Primary Examiner*—Carlos Azpuru
*Attorney, Agent, or Firm*—Patterson & Keough, P.A.

[57] ABSTRACT

A method of treating involuntary muscle dysfunctions includes administering a therapeuticaly effective amount of relaxin to a patient. Involuntary muscle dysfunctions amenable to treatment with relaxin include fibromyalgia, myofascial pain syndrome, chronic fatigue syndrome, dystonia, pelvic floor dysfunction, irritable bowel syndrome, and others.

3 Claims, No Drawings

OTHER PUBLICATIONS

A.M. Poisner et al., "Relaxin Stimulats The Synthesis and Release of Prorenin from Human Decidual Cells: Evidence for Autocrine/Paracrine Regulation", Journal of Clinical Endocrinology and Metabolism, vol. 70, No. 6, pp. 1765–1767, 1990.

E. Bullesbach et al., "Total Synthesis of Human RElaxin and Human RElaxin Derivatives by Solid–phase Peptide Synthesis and Site–directed Chain Combination", The Journal of Biological Chemistry, vol. 266, No. 17, Issue of Jun. 15, pp. 10754–10761, 1991.

M.B. O'Day–Bowman et al., Hormonal Control of the Cervix in Pregnant Gilts. III. Relaxin's Influence on Cervical Biochemical Properties in Ovariectomized Hormone–Treated Gilts, Endocrinology, 1991, vol. 129, No. 4, pp. 1967–1976.

Letten F. Saugstad, "Persistent Pelvic Pain and Pelvic Joint Instability", European Journal of Obstetrics & Gynecology and Reproductive Biology, vol. 41, 1991, pp. 197–201.

Erika Bullesback et al., The Receptor–Binding Site of Human Relaxin II, The Journal of Biological Chemistry, vol. 267, No. 32, Issue of Nov. 15, pp. 22957–22960, 1992.

Jeffrey A. Hall et al., "Influence of Ovarian Steroids on Relaxin–Induced Uterine Growth in Ovariectomized Gilts". Endocrinology. 1992, vol. 130, No. 6, pp. 3159–3166.

Douglas Kibblewhite et al., "The Effect of Relaxin on Tissue Expansion", Arch. Otolaryngol Head Neck Surg.. vol. 118, Feb. 1992, pp. 153–156.

A.B. Lee et al., "Monoclonal Antibodies Specific for Rat Relaxin. IV. Passive Immunization with Monoclonal Antibodies throughout the Second Half of Pregnancy Disrupts Histological Changes Associated with Cervical Softening at Parturition in Rats", Endocrinology. 1992. vol. 130, No. 4, pp. 2386–2391.

Robin J. Bell et al., "A Randomized. Double–Blind. Placebo–Controlled Trial of the Safety of Vaginal Recombinant Human Relaxin for Cervical Ripening", Obstetrics & Gynecology, vol. 82, No. 3. Sep. 1993. pp. 328–333.

Gillian D. Bryant–Greenwood et al., "Sequential Appearance of RElaxin. Prolactin and IGFBP–1 During Growth and Differentiation of the Human Endometrium", Molecular and Cellular Endocrinology, vol. 95, 1993, pp. 23–29.

Sharon A. Chen et al.. "The Pharmacokinetics of Recombinant Human Relaxin in Nonpregnant Women After Intravenous, Intravaginal. and Intracervical Administration", Pharmaceutical Research. vol. 10. No. 6, 1993 pp. 834–838.

C. Huang, et al., "Stimulation of Collagen Secretion by Relaxin and Effect of Oestrogen on Relaxin Binding in Uterine Cervical Cells of Pigs", Journal of Reproduction and Fertility, 1993, vol. 98. pp. 153–158.

Phyllis L. Osheroff et al., "Expression of Relaxin mRNA and Relaxin Receptors in Postnatal and Adult Rat Brains and Hearts", The Journal of Biological Chemistry, vol. 268, No. 2, Issued Jul. 15, pp. 15193–15199, 1993.

Pramod R. Saxena et al., "Cardiac Effects of Relaxin", TiPS, Jun. 1993, vol. 14, pp. 231–232.

Don L. Goldenberg, "Medications/Clinical Trials in Fibromyalgia", Journal of Musculoskeletal Pain, vol. 2, No. 3, 1994, pp. 135–142.

Frederick Wolfe, MD, "When to Diagnose Fibromyalgia", Diagnostic Issues: 20/2, 1994, pp. 485–501.

Yunus et al., "Primary Fibromyalgia Syndrome and Myofascial Pain Syndrome: Clinical Features and Muscle Pathology", Arch Phys Med Rehabil, vol. 69, Jun. 1988.

Bruce Rothschild et al., "Retrospective Assessment of Fibromyalgia Therapeusis", Comprehensive Therapy, 1994, vol. 20(10): pp. 545–549.

Frederick Wolfe, "Post–traumatic Fibromyalgia: A Case Report Narrated by the Patient", Arthritis Care and Research, vol. 7(3), pp. 161–165, Sep. 1994.

Testimony to the U.S. Senate Appropriations Subcommittee on Labor, Health & Human Services, and Education, Mar. 31, 1995.

Patient Information Sheet, ILETIN® I, II, III, Eli Lilly and Company, 1989, 5 pages.

Patient Information Sheet, HUMULIN® R, 5 pages, Jul. 1994.

Patient Information Sheet, HUMULIN® L, 4 pages, Jul. 1994.

Patient Information Sheet, HUMULIN® N, 4 pages, Oct. 1994.

Patient Information Sheet, Novolin® R, 4 pages, Dec. 1993.

Patient Information Sheet, Novolin® N, 4 pages, Dec. 1993.

Patient Information Sheet, Catapres–TTS®, 6 pages, Oct. 1992.

Patient Information Sheet, Estraderm®. Rev. Dec. 1992, 2 pages.

Patient Information Sheet, Transderm–Nitro® Rev. Oct. 1989, 3 pages.

Patient Information Sheet, Prochlorperazine Suppositories, USP, 4 pages. Jul. 1993.

Patient Information Sheet, TERAZOL® 3, Rev. Feb. 1991. Ortho Pharmaceutical Corporation, 4 pages, Feb. 1991.

Patient Information Sheet, MONISTAT® 7, Rev. Nov. 1992, Advanced Care Products, 3 pages.

Patient Information Sheet, Hydrocortisone Acetate Suppositories 25 mg. Paddock Laboratories. Inc., Oct. 1994.

Karl G. Henriksson, "Pathogenesis of Fibromyalgia", Journal of Musculoskeletal Pain, vol. 1, No. 3/4, 1993. pp. 3–16.

Alfonse T. Masi, "Review of the Epidemiology and Criteria of Fibromyalgia and Myofascial Pain Syndromes: Concepts of Illness in Populations as Applied to Dysfunctional Syndromes", Journal of Musculoskeletal Pain. vol. 1, No. 3/4, 1993, pp. 113–136.

Israel A. Posner, "Treatment of Fibromyalgia Syndrome with Intravenous Lidocaine: A Prospective, Randomized Pilot Study", Journal of Musculoskeletal Pain. vol. 2(4). 1994, pp. 55–65.

Robert M. Bennett, "Fibromyalgia Review", Journal of Musculoskeletal Pain. vol. 2(4). 1994, pp. 99–112.

Russell I. Jon, "Foreword: NIH Conference on Fibromyalgia", Journal of Musculoskeletal Pain, vol. 2, No. 3, 1994 pp. xiii–xv.

Muhammad B. Yunus, "Fibromyalgia Syndrome: Clinical Features and Spectrum", Journal of Musculoskeletal Pain. vol. 2, No. 3, 1994, pp. 5–21.

Frederick Wolfe, "Fibromyalgia: On Criteria and Classification", Journal of Musculoskeletal Pain, vol. 2. No. 3. 1994, pp. 23–39.

Frederick Wolfe, "Aspects of the Epidemiology of Fibromyalgia", Journal of Musculoskeletal Pain, vol. 2, No. 3, 1994, pp. 65–77.

I. Jon Russell, "Biochemical Abnormalities in Fibromyalgia Syndrome", Journal of Musculoskeletal Pain, vol. 2, No. 3, 1994, pp. 101–115.

R.J. Winn et al., "Individual and Combined Effects of Relaxin, Estrogen, and Progesterone in Ovariectomized Gilts. II. Effects on Mammary Development", Endocrinology, 1994, vol. 135, No. 3, pp. 1250–1255.

Gillian D. Bryant–Greenwood et al., "Human RElaxins: Chemistry and Biology", Endocrine Reviews, vol. 15, No. 1, pp. 5–26, 1994.

MR Johnson et al., "Relationship Between Ovarian Steroids, Gonadotrophins and Relaxin During the Menstrual Cycle", Acta Endocrinologica 1993, vol. 129, pp. 121–125.

KJ Berkley et al., "Muscle Pain Thresholds in Dysmenorrheic Versus Normal Women: Variations as a Function of Segmental Site and Monthly Cycle", Abstract from the 3rd Wrold Congress on Myofascial Pain & Fibromyalgia San Antonio, Tx. Jul. 30–Aug. 3, 1995.

Masi, Alfonse T., "Review of the Epidemiology and Criteria of Fibromyalgia and Myofascial Pain Syndromes: Concepts of Illness on Populations as Applied to Dysfunctional Syndromes," Journal of Musculoskeletal Pain, vol. 1, No. 3/4, 1993, pp. 113–136.

METHOD OF COLLAGEN THERAPY USING RELAXIN

This is a Divisional Application of application Ser. No. 09/005,383, filed Jan. 9, 1998 now U.S. Pat. No. 5,863,552, which in turn is a division of application Ser. No. 08/802, 340, filed Feb. 11, 1997, now U.S. Pat. No. 5,707,642, which in turn is a continuation of application Ser. No. 08/560,492, filed Nov. 17, 1995, which issued as U.S. Pat. No. 5,612,051 on Mar. 18, 1997.

BACKGROUND OF THE INVENTION

The present invention relates to the treatment of involuntary muscle dysfunctions. In particular, the present invention relates to the treatment of involuntary muscle dysfunction with relaxin hormone.

Involuntary muscle dysfunction plagues a large portion of the chronic pain and chronic fatigue patient population. Two prominent conditions involving involuntary muscle dysfunction include fibromyalgia and myofascial pain syndrome, amongst others.

Fibromyalgia is identified by the main symptoms of generalized chronic pain occurring mainly in the muscles and hyperalgesia, i.e. multiple tender points spread out over the body. The full range of symptoms include generalized pain, hyperalgesia, sleep disturbance, fatigue, muscle stiffness, hypersthesias, tension-type headaches, decreased muscle endurance and muscle weakness. Fibromyaglia has also been associated with irritable bowel syndrome, chronic fatigue syndrome, temporomandibular dysfunction syndrome, migraines, primary dysmenhorrea (painful menstruation) and others conditions including Raynaud's phenomenon. See Yunnus, *Fibromyalgia Syndrome: Clinical Features and Spectrum,* The Fibromyalgic Syndrome: Current Research and Future Directions in Epidemiology, Pathogenesis, and Treatment, 1994, pp. 5–21. See also Wolfe, *When to Diagnose Fibromyalgia,* Rheumatic Disease Clinics Of North America, Vol. 20, Number 2, May 1994. See Henriksson, *Pathogenesis of Fibromyalgia,* Journal of Musculoskeletal Pain, 1993, Vol. 1, pp. 3–16.

Fibromyalgia is the second or third most common disorder seen in community practice. The economic effects of fibromyalgia are substantial. In one study, it was reported that only 60% of fibromyalgia patients were employed, 30% of patients changed jobs because of fibromyalgia, 10% of patients considered themselves disabled, and 6% received disability payments. See Rothschild et al, *Retrospective Assessment of Fibromyalgia Therapeusis,* Comprehensive Therapy 1994, Vol. 20, pp 545–549.

Fibromyalgia also appears to be concentrated amongst the female patient population. It is estimated that about 80 to 90% of fibromyalgia patients are women. In addition, most patients are reported to fall in the 40 to 50 year age range. However, some studies have identified an archetypical patient as being a young women between the ages of 20 and 40. See Masi, A., *Review of The Epidemiology and Criteria of Fibromyalgia and Myofascial Pain Syndromes: Concepts of Illness in Populations as Applied to Dysfunctional Syndromes,* Journal of Musculoskeletal Pain, 1993, Vol. 1, pp. 113–116. See also Yunnus, supra, page 6.

While there is no current cure for fibromyalgia, it has been reported that some patients have responded to therapy with Halcion® and hypnosis. See Rothschild et al. However, these treatment modalities primarily address sleep disturbance and do not squarely address the cause of fibromyalgia or its full range of symptoms. Moreover, the use of Halcion® is not suitable for long-term treatment. While Halcion® induces sleep, Halcion also inhibits the patient's ability to achieve rapid eye movement (REM) sleep, which is necessary for therapeutic sleep.

Other conventional treatments of fibromyalgia include treating localized pain and muscle tension with intramuscular application of botulinum toxin as well as treatments including relaxation medication, exercise, and physical therapy. These latter treatment methods are aimed at relaxing and elongating the affected muscles.

However, none of these previous attempts at alleviating the symptoms of fibromyalgia and related involuntary muscle dysfunctions are effective. Moreover, these methods do not address the cause of fibromyalgia and other involuntary muscle dysfunctions.

In addition, many patients suffer from one or several of the symptoms (e.g., dysmenorrhea) associated with fibromyalgia without actually having fibromyalgia or the full range of symptoms. No single treatment is currently available for treating most or all of these symptoms.

SUMMARY OF THE INVENTION

The present invention is based on the recognition that the involuntary muscle dysfunctions associated with fibromyalgia, myofascial pain syndrome, dystonia, chronic fatigue syndrome, and other condition is the result of a deficiency of relaxin hormone or a suppression of relaxin's effect in the bloodstream. This lack of relaxin in the blood stream may be congenital or the result of another mechanism which suppresses the normal production or action of relaxin. Accordingly, a method of the present invention of treating involuntary muscle dysfunction comprises administering to a patient exhibiting symptoms associated with these conditions a therapeutically effective amount of relaxin hormone. The relaxin hormone will alleviate these conditions since relaxin acts to effect collagen formation and remodelling, thereby causing tissue changes of the type associated with parturition, i.e., smooth muscle relaxation, elongation of tendons and ligaments, etc.

This recognition is based on clinical observations by the inventor of the symptoms reported by female patients with fibromyalgia or myofascial pain syndrome when these patients are pregnant or in menopause. In particular, the basic observation is that fibromyalgia patients and myofascial pain syndrome patients do not report or exhibit the same symptoms (generalized pain, fatigue, inflexibility) when they are pregnant that they report or exhibit when they are not pregnant. In short, many or all of the symptoms associated with these conditions (e.g., fibromyolgia, myofascial pain, etc.) disappear when these patients are pregnant. Specifically, a large number of fibromyalgia patients (and patients with other involuntary muscle dysfunction maladies) report that their pain-related symptoms subside during pregnancy and return after pregnancy. This relationship is significant since the vast majority of fibromyalgia patients are women. The disappearance of fibromyalgia symptoms in these patients when pregnant is explained by the relatively high elevation of relaxin during pregnancy.

This recognition of relaxin as the primary causal agent in involuntary muscle dysfunction is confirmed by clinical observations by the inventor of patients with premenstrual pain syndrome (PMS). Women that have fibromyalgia or myofascial pain syndrome frequently have dysmenorrhea, reporting that their symptoms are aggravated just before and during the menstrual period. It is known in the art that the level of relaxin typically rises in women about 7–10 days after the midcycle surge of the luteinizing hormone and when conception does not occur, the level falls precipitously about one week before the menstrual period begins. The inventor has observed that female patients with PMS, fibromyaglia or myfascial pain syndrome with dysmenorrhea, all report an increase or beginning of their painful symptoms and muscle tension and discomfort one week before and during the menstrual period. Specifically, the inventor has observed that the precipitously falling level of the circulating relaxin corresponds to the beginning or increase in the level of patients' pain and discomfort one week before and during the menstrual period.

Administering relaxin to patients with fibromyalgia, myofascial pain syndrome and related involuntary muscle dysfunctions is expected to significantly alleviate the core symptoms of these conditions, e.g., generalized pain and tenderness, as well as alleviate specific secondary symptoms such as dysmenorrhea.

DETAILED DESCRIPTION OF THE PREFERRED EMBODIMENTS

I. Definition of Relaxin

Relaxin has been extensively documented regarding its presently known structure, functions, and properties. See Bryant-Greenwood et al., *Human Relaxin: Chemistry and Biology,* Endocrine Reviews, Vol. 15, No. 1, (1994), and the articles cited therein.

Relaxin has been well defined in its natural human form, animal form, and in its synthetic form. In particular, relaxin has been extensively described in Cronin et. al. U.S. Pat. No. 5,166,191 and Burnier et. al. U.S. Pat. No. 4,835,251, both of which are hereby incorporated by reference. In this application, "relaxin" generally refer to the terms "relaxin", "human relaxin", "native relaxin", and "synthetic relaxin" as defined in U.S. Pat. No. 5,166,191 and the terms "human relaxin" and "human relaxin analogs" as defined in U.S. Pat. No. 4,835,251. "Relaxin" in this application will also refer to relaxin as isolated in pigs, rats, horses and relaxin produced by recombinant techniques based cDNA clones for rat porcine relaxin.

Methods of making relaxin and its analogs are known in the art. In addition, methods for isolating and purifying relaxin are known in the art. Several sources for these methods are identified in U.S. Pat. No. 5,166,191 including the following references: U.S. Pat. No. 4,835,251, Barany et al., *The Peptides* 2, 1 (1980), Treager et al., *Biology of Relaxin and its Role in the Human,* pp. 42–55; EP 251,615; EP 107,782; EP 107,045; and WO 90/13659.

II. Pregnancy Associated Physiologic Changes Produced by Relaxin

Relaxin has long been associated with pregnancy and parturition, showing a marked increase during pregnancy in women and other female species (e.g. rats, pigs). Relaxin is well known as an agent for remodelling the reproductive tract via collagen remodelling before parturition, thereby facilitating the birth process.

Relaxin is known to increase in peripheral plasma 7–10 days after the midcycle surge of luteinizing hormone and continues to rise to over 800 pg/ml by three weeks if conception occurred. During pregnancy, relaxin levels peak at the 10th week and are maintained at about 500 pg/ml for the remainder of the pregnancy.

During pregnancy, relaxin remodels the reproductive tract which includes ripening of the cervix, thickening of the endometrium of the uterus, increasing vascularization of the uterus, and affecting collagen synthesis to cause ligaments and connective tissue to elongate and relax. It has also been observed that Raynaud's lesions completely disappear during early pregnancy. This observation has been loosely associated with the elevation of circulating relaxin. There also have been reports on relaxin's effect on cardiac output and specifically relaxin's ability to increase the rate of contraction of the right atrium and force of contraction of the left atrium of the heart. See Cronin, U.S. Pat. No. 5,166,191.

Systemic relaxin is known to produce physiologic changes in collagen activity and consequential tissue remodelling. This collagen activity is associated with elongation of connective tissue. Systemic relaxin is also known to produce physiologic responses in smooth muscle. In particular, porcine relaxin has been shown to inhibit contractions of cervical smooth muscle in pregnant women. See Bryant-Greenwood et al., *Human Relaxins: Chemistry and Biology,* Endocrine Reviews, Vol. 15., No. 1, (1994).

It is also known that the pharmacologic activity of relaxin is related to the presence of estradiol, progesterone, and hCG, with the presence of estradiol and progesterone being correlated with relaxin synthesis and elevation. See Johnson et al. *Relationship Between Ovarian Steroids, Gonadotrophins, and Relaxin During the Menstrual Cycle,* Acta Endocrinologica, Vol. 129:121–125 (1993). See also Bryant-Greenwood et al.

III. Explanation Of Expected Therapeutic Effect of Relaxin on Involuntary Muscle Dysfunction

A. Basic Clinical Observations Regarding Relaxin

The present invention is based on the inventor's recognition that the involuntary muscle dysfunctions associated with fibromyalgia, myofascial pain syndrome, dystonia, chronic fatigue syndrome, and other conditions is the result of a deficiency of relaxin hormone in the bloodstream. This lack of relaxin in the blood stream may be congenital or the result of another mechanism which suppresses the normal production of relaxin. Accordingly, a method of the present invention of treating involuntary muscle dysfunction comprises administering to a patient exhibiting symptoms associated with these conditions a therapeutically effective amount of relaxin hormone.

The relaxin hormone will alleviate these conditions since relaxin acts to effect collagen formation and collagen remodelling. Relaxin will alleviate the generalized pain and tenderness by elongating muscles and accentuating joint laxity by remodelling connective tissue (e.g ligaments, tendons, bone, etc.) via collagen chances. This expected effect is based on many studies that have observed that pregnant women have elongated pelvic area muscles, and increased joint laxity resulting from the remodelling effect induced by relaxin.

This recognition is based on clinical observations by the inventor of the symptoms reported by female patients with fibromyalgia or myofascial pain syndrome when these patients are pregnant or in menopause. In particular, the basic observation is that fibromyalgia patients and myofascial pain syndrome patients do not report or exhibit the same symptoms (generalized pain, fatigue, inflexibility) when they are pregnant that they report when they are not pregnant. In short, many or all of the symptoms associated with these conditions disappear when the patients are pregnant. These female fibromyalgia patients also report an aggravation of their symptoms after menopause. These relationships are significant since the vast majority of fibromyalgia patients are women.

This disappearance of symptoms of fibromyalgia in these patients when pregnant is believed by the inventor to be explained by the relatively high elevation of relaxin during pregnancy. Specifically, a large number of fibromyalgia patients (and patients with other involuntary muscle dysfunction maladies) report that their pain-related symptoms subside during pregnancy and return after pregnancy.

This recognition of relaxin as the primary causal agent in involuntary muscle dysfunction is confirmed by clinical observations by the inventor of patients with premenstrual pain syndrome (PMS). Women that have fibromyalgia or myofascial pain syndrome report that their symptoms are aggravated just before and during the menstrual period. It is known in the art that the level of relaxin typically rises in women about 7–10 days after the midcycle surge of the luteinizing hormone and when conception does not occur, the level falls precipitously about one week before the menstrual period begins. The inventor has observed that female patients with PMS, fibromyaglia or myfascial pain syndrome with dysmenorrhea, all report an increase or beginning of their painful symptoms and muscle tension and discomfort one week before and during the menstrual period. Specifically, the inventor has observed that the precipitously falling level of the circulating relaxin corresponds to the beginning or increase in the level of patients' pain and discomfort one week before and during the menstrual period.

Moreover, the clinical observation of aggravation of fibromyalgia symptoms in post menopausal women is believed to result from the shutdown of reproductive organs that ordinarily produce relaxin. In these women, the inventor believes that whatever minimal amount of relaxin that was being produced completely subsides by menopause.

Based on these clinical observations, the inventor believes that fibromyaglia is a rheumatologic disease which results from a deficit of relaxin. This lack of relaxin affects collagen chances so that muscle spindles on the striated and smooth muscles are much shorter than they otherwise would be. This results in increased muscle tone and the accompanying symptoms of pain, fatigue, and tenderness.

B. Congenital or Trauma Induced Involuntary Muscle Dysfunction

One class of fibromyalgia patients have generalized pain and other symptoms starting from their teenage years. The inventor believes that these patients suffer due to a congenital maldevelopment of the organs (e.g ovary) or other sites that produce relaxin, which in turn inhibits or suppresses relaxin production. The beginning of fibromyalgia is likely marked by menarche (beginning of menstruation). In teenage patients, the pain is generalized overall and increases in intensity as the patient gets bigger and acquires more musculature. As these patients mature, these patients are in constant pain when in a non-pregnant state yet have almost no generalized pain symptoms when pregnant. However, the classic symptoms return when the pregnancy is over.

Another class of fibromyalgia patients have musculatures that operate sufficiently until certain trauma precipitate a muscle spasm or involuntary muscle event resulting in pain, fatigue, and tenderness. The inventor believes that after this event, these patients bodies are unable to reverse the process due to a congenitally low level of relaxin or chronic suppression of this hormone.

Unlike fibromyalgia, the inventor believes that myofascial pain syndrome is not congenitally based but rather is associated with aging. In particular, our musculature may require more relaxin as we age to lubricate itself, i.e., to maintain flexibility and relaxation. Relaxin can be viewed as a lubricant on the body allowing collagen to remodel itself, thereby permitting the musculature and connective tissue to continue to function like a young person's musculature. Alternatively, normal production of relaxin may decrease as we age, thereby necessitating relaxin supplementation to maintain muscle relaxation and connective tissue flexibility.

C. Relaxin Action on Smooth Muscle Dysfunctions: Gastrointestinal, Urinary, and Pelvic Dysfuctions While the administration of relaxin to fibromyalgia and myofascial pain patients is expected to alleviate the core symptoms of generalized pain, hyperalgesia (multiple tender points), and inflexibility, the inventor also believes that relaxin will have a substantial effect on related symptoms involving smooth muscle dysfunction.

Fibromyaglia patients also have other symptoms related to smooth muscle control including gastrointestinal tract difficulties, urinary tract difficulties, and pelvic dysfunctions. Gastrointestinal difficulties include bowel and intestinal dysfunction while urinary dificulties include bladder and urethral dysfunctions.

Regarding bowel dysfunction, fibromyalgia patients frequently have a condition known as spastic colon (i.e., irritable bowel syndrome), which results from high tone in the smooth muscles controlling the gastrointestinal tract. These patients can exhibit constipation, obstruction, diarrhea, and other gastrointestinal symptoms. In these patients, the intestines and colon becomes so constricted that they perform an all or nothing response. In this situation, no bowel movement occurs because the constriction results in constipation. When the constriction is released, it does so in an abrupt manner resulting in diarrhea. Accordingly, patients with a spastic colon suffer from constipation alternating with diarrhea.

The inventor believes that this smooth muscle bowel dysfunction is related to a lack of relaxin. In particular, since these conditions result from the GI tract, which is regulated by smooth muscle activity, it is believed that relaxin can be used to diminish the abnormally high muscle tone associated with a spastic colon.

Two other common problems associated with fibromyalgia include urinary difficulty and vaginismus. Urinary difficulty results from tight sphincter muscle tone on the bladder while vaginismus is extra tight contraction of the vagina when these muscles go into spasm. This can result in difficulty during sexual intercourse, passing stool, and passing urine. Pelvic floor myalgia or pelvic floor dysfunction including dysfunctions in micturition (urination), evacuation of the bowel, and sexual functions are believed to be treatable with relaxin because of relaxin's effect on smooth muscle. In particular, the inventor believes that relaxin will reduce the amount of tone exhibited by the smooth muscles regulating these activities.

Finally, the inventor believes that premenstrual syndrome (PMS) is a subclinical form of myofascial pain syndrome with obvious pelvic floor congestion and dysfunction, irritable bowel syndrome and hyperactive uterus. All of these symptoms are related to high smooth muscle tone and activities and appear a week before and during the menstrual period. Therefore, these reactive events within the pelvic floor are related to the precipitous fall of the relaxin level prior to the menstrual period. Based on this clinical observation, the inventor believes that these symptoms should be alleviated with relaxin which would relax the smooth muscles affecting those pelvic functions.

In addition to muscle pain and dysfunction in the reproductive tract region, dysmenorrheic women also have heightened sensitivity to pain in unrelated regions of the body (e.g., deltoid muscle and quadriceps muscle). See Berkley et al., *Muscle Pain Thresholds In Dysmenorrheic Versus Normal Women: Variations as a Function of Segmental Site and Monthly Cycle,* Abstract 3rd World Congress on Myofascial Pain & Fibromyalgia. San Antonio, Tex., 1995. The inventor believes the heightened sensitivity to pain in the nonreproductive regions is due to a lack of relaxin in these dysmenorrheic women and that administration of relaxin can alleviate these symptoms sometimes associated with fibromyalgia and myofascial pain syndrome.

D. Raynaud's Phenomenon

Relaxin is known to affect smooth muscle. In particular, it is known that relaxin can cause dilation of blood vessels through its action on the smooth muscle of the blood vessel, which in turn slows down the constrictive activity of smooth muscles. This effect is consistent with the clinical observations made by the inventor of pregnant involuntary muscle dysfunction patients and the expected effect of relaxin. For example, relaxin has been associated with an alleviation of Raynaud's phenomenon, which is a vasospastic disease in which blood vessels become very tight when exposed to cold weather. This phenomenon is regulated by a hyperreactive smooth muscle of the blood vessels. As observed by the inventor, these symptoms disappear when these involuntary muscle dysfunction patients are pregnant. The inventor believes that the disappearance of these symptoms is directly related to the relatively high levels of relaxin obsessed in pregnant women.

E. Chronic Fatigue Syndrome and Other Conditions

Chronic fatigue syndrome is a different manifestation of fibromyalgia. In particular, it is believed that in fibromyalgia the primary manifestation of a lack of relaxin is pain with muscle fatigue as a secondary manifestation and that in chronic fatigue syndrome, muscle fatigue is the primary manifestation of a lack of relaxin with pain being secondary. Chronic fatigue syndrome results from the muscles fatiguing prematurely from operating inefficiently. Extra efforts are required to initiate contraction of the stiff striated muscles causing an excessive amount of fatigue. The inventor believes that this inefficient muscle operation and associated muscle fatigue results from a congenital lack of relaxin.

Other trauma, such as removal of the ovary or glandular problems in the male might inhibit the production of relaxin, and thereafter acquire a relaxin deficit and present patients with fibromyalgia like symptoms.

F. Treatment of Smooth Muscle Dysfunction and Other Conditions Without Fibromyalgia or Myofascial Pain Syndrome While the treatment of fibromyalgia and the explanation for the expectation of relaxin to alleviate its symptoms has been previously discussed, the inventor also believes that relaxin can be administered as a supplement for patients not having fibromyalgia (or myofascial pain syndrome) to treat any of one of the symptoms previously discussed. For example, some women may have PMS or may have a spastic colon without other symptoms of fibromyalgia or myofascial pain syndrome. For these patients, relaxin would be expected to still alleviate the symptoms by acting to decrease high tone smooth muscle activity causing the dysfunction and discomfort. It is believed that relaxin replacement or supplementation can also treat fibromyalgia-like symptoms in males.

Moreover, additional benefits of relaxin's effect on collagen can be achieved. For example, relaxin can be applied topically to the epidermis to cause collagen remodelling, thereby increasing the elasticity and function of the skin. Another example would be the infusion of a therapeutic level of relaxin to abort the pain associated with vasospastic events of the body and vasomotor events within the cranium.

G. Specific Pharmacologic Activity of Relaxin

The inventor believes that the necessary pharmacologic activity of relaxin on the tissues of the body for treating the symptoms of involuntary muscle dysfunction and related conditions as claimed herein is established by the references cited herein and further including the following references: MacLennan A H, et al., *Ripening of the Human Cervix and Induction of Labor with Intracervical Purified Porcine Relaxin,* Obstretics & Gynecology (1986) Vol. 68, No. 5, pp. 598–601; Poisner A M, et al., *Relaxin Stimulates the Synthesis and Release of Prorenin From Human Decidual Cells: Evidence For Autocrine/Paracrine Regulation,* J of Clinical, Endocrinology an Metabolism (1990) Vol. 70, No. 6, pp 1765–1767; O'Day-Bowman M B, et al. *Hormonal Control of the Cervix in Pregnanet Gilts. III. Relaxins's Influence on Cervical Hiochemical Properties in Ovariectomozed Hormone-Treated Pregnant Gilts,* Endocrinology (1991) Vol. 129, No. 4, pp. 1967–1976; Saugstad L F, *Persistent Pelvic Pain and Pelvis Joint Instability,* Euro Journal of Obstretics & Gynecology and Reproductive Biology (1991) 41, 197–201; Bullesbach E E, et al., *The Receptor-Binding Sites of Human Relaxin II,* The Journal of Biological Chemistry (1992) Vol. 267, No. 32, pp. 22957–22960; Hall J A, et al., *Influence of Ovarian Steroids or Relaxin-Induced Uterine Growth in Ovariectomized Gilts,* Endocrinology (1992) Vol. 130, No. 6, 3159–3166; Kibblewhite D. et al., *The Effect of Relaxin on Tissue Expansion,* Arch Otolaryngol Head Neck Surg. (1992) Vol. 118, pp. 153–156; Lee A B, et al., *Monoclonal Antibodies Specific for Rat Relaxin. VI. Passive Immunization with Monoclonal Antibodies Throughout the Second Half of Preganncy Disrupts Histological Changes Associated with Cervical Softening at Parturition in Rats,* Endocrinology (1992) Vol. 130, No. 4, pp. 2386–2391; Bell R J, et al., *A Randomized, Double-Blind Placebo-Controlled Trial of the Safety of Vaginal Recombinant Human Relaxin for Cervical Ripening,* Obstretics & Gynecology (1993) vol. 82, No. 3, PP.328–333; Bryant-Greenwood G D, et al., *Sequential Appearance of Relaxin, Prolactin and IGFBP-1 During Growth and Differentiation of the Human Endometrium,* Molecular and Cellular Endocrinology (1993) 95, pp. 23–29; Chen S A, et al., *The Pharmacokinetics of Recombinant Human Relaxin in Nonpregnant Women After Intravenous, Intravaginal, and Intracervical Administration,* Pharmaceutical Research (1993) Vol. 10, No. 6, pp 834–838; Huang C. et al., *Stimulation of Collagen Secretion by Relaxin and Effect of Oestrogen on Relaxin Binding in Uterine Cervical Cells of Pigs,* Journal of Reproduction and Fertility (1993) 98, 153–158; Saxena P R, et al., *Is the Relaxin System a Target for Drug Development? Cardiac Effects of Felaxin,* TiPS (June 1993) Vol. 14, pp. 231, letter; Winn R J, et al., *Hormonal Control of the Cervix in Pregnant Gilts. IV. Relaxin Promotes Changes in the Histological Characteristics of the Cervix that are Associated with Cervical Softening During Late Pregnancy in Gilts,* Endocrinology (193) Vol. 133, No. 1, pp. 121–128; Colon J M, et al., *Relaxin Secretion into Human Semen is Independent of Gonadotropin Stimulation,* Biology of Reproduction (1994) 50, pp. 187–192; Golub M S, et al., *Effect of Short-Term Infusion of Recombinant Human Relaxin on Blood Pressure in the Late-Pregnant Rhesus Macaque (Macaca Mulatta),* Obstretics & Gynecology (January 1994) Vol. 83, No. 1, pp. 85–88; Jauniaux E. et al., *The Role or Relaxin in the Development of the Uteropla-* cental Circulation in Early Pregnancy, Obstetrics & Gynecology (1994) 84(3): 338–342; Johnson M R, et al., *The Regulation of Plasma Relaxin Levels During Human Pregnancy,* Journal of Endocrinology (1994) 142,261–265; Lane B, et al., *Decidualization of Human Endometrial Stromal Cells in Vitro: Effects of Progestin and Relaxin on the Ultrastructure and Production of Decidual Secretory Protein,* Human Reproduction (1994) Vol. 9, No. 2, pp. 259–266; Lanzafame F, et al., *Pharmacological Stimulation of Sperm Motility,* Human Reproduction (1994) Vol. 9, No. 2, pp. 192–199; Petersen K L, et al., *Normal Serum Relaxin in Women with Disabling Pelvic Pain During Pregnancy,* Gynecol Obstet Invest (1994) 38: 21–23; Tashima L S, et al., *Human Relaxins in Normal, Benign and Neoplastic Breast Tissue,* Journal of Molecular Endocrinology (1994) 12, 351–364; Winn R J, et al. *Individual and Combined Effects of Relaxin, Estrogen, and Progesterone in Ovaroective Gilts. I. Effects on the Growth, Softening, and Histological Properties of the Cervix,* Endocrinology (1994) Vol. 135, No. 3, pp. 1241–1249; Winn R J, et al., *Individual and Combined Effects of Relaxin, Estrogen, and Progesterone on Ovariectomized Gilts. II. Effects on Mammary Development,* Endocrinology (1994) Vol. 135, No. 3, pp. 1250–1255; Bryant-Greenwood G D, et al., *Human Relaxins: Chemistry and Biology,* Endocrine Reviews (1994) 15:1; p.5–26; Johnson M R, et al., *Relationship Between Ovarian Steriods, Gonadotrophins and Relaxin During the Menstral Cycle,* Acta Endocrinilogica (1993) 129: 121–5.

IV. Method of Administration and Dose

Relaxin is known to be structurally similar to insulin. See Burnier et al., U.S. Pat. No. 4,835,251. Accordingly, relaxin is expected to be introducible into the body in a manner substantially similar to insulin. Relaxin and its analogs can be formulated using known methods to prepare pharmaceutically useful compositions by combining relaxin with a pharmaceutically acceptable carrier. Suitable carriers and their formulation are known in the art. See also U.S. Pat. No. 4,835,251.

Currently known techniques of subcutaneous administration of insulin can be used to administer natural relaxin. For example, it is expected that relaxin can be administered by a carrier and formulation similar to an insulin zinc suspension sold by Eli Lilly of Indianapolis Ind. under the trademark LENTE® ILETIN®. This product is an amorphous and crystalline suspension of insulin with zinc providing an intermediate acting insulin with a slower onset and a longer duration of activity (slightly more than 24 hours) than regular insulin. The duration of action, of course, being dependent on dose, site of injection, blood supply, temperature and physical activity. Similarly, for synthetic relaxin, it is expected that a formulation like HUMULIN® for insulin of recombinant DNA origin would be well suited to act as a carrier.

Insulin carriers come in several different standard formulations to achieve a desired duration of administration. These standards include: R (regular, short duration action), N (NPH, human insulin injection, intermediate duration activity), LENTE® (e.g., long duration activity) and UL (ultra long duration activity).

Other methods of introducing relaxin can include transdermal patch application in which small amounts of a drug are continuously released into the skin, and ultimately the bloodstream. This method of administration is used when a moderate volume of relaxin is to be administered over a long period of time, e.g. one to four weeks. Examples of transdermal applications expected to be suitable for administering relaxin include an estrogen product (estradiol transdermal system) sold under the trademark ESTRADERM® and a nitroglycerin transdermal product sold under the name TRANSDERM-NITRO®, and a clonidine transdermal therapeutic system sold under the trademark CATAPRES-TTS®. For example, the CATAPRESS-TTS® brand patch includes four components which together result in controlled release of colindine into the skin and bloodstream.

Finally, relaxin can be applied vaginally or rectally by using a suppository as a drug delivery vehicle. For example, relaxin can be incorporated into suppository system like a rectal suppository sold under the trade name PROCHLORPERAZINE® suppositories or like a vaginal suppository sold under the trademark MONISTAT 7® (used for administering miconazole nitrate).

A therapeutically effective amount defines an amount resulting in the improvement of a physiologic condition to be treated. The actual dose will be different for the various specific physiologic conditions and molecules, and will vary with the patients overall condition, the seriousness of the symptoms, contraindications, etc. The determination of the effective dose is well within the skill of a practicing physician.

For comparison purposes, relaxin can be administered in cardiovascular applications (See U.S. Pat. No. 5,166,191) in the form of pharmaceutical formulations having an effective amount of relaxin in a buffer with a pH of 4–7, preferably 4.5–5.5. One example of an acceptable formulation for a cardiovascular application includes human relaxin in an 10 nM citrate buffer at pH 5 with sodium chloride present to a total ionic strength of about 0.15 $\mu$, representing the proper osmolality. Also in the cardiovascular context, a typical subcutaneous dose range for the treatment of human patients is about 1.5 $\mu$g to about 0.15 mg/kg of body weight/day.

Of course the dose for treating involuntary muscle dysfunction depends on several factors including the route of administration, formulation method, patient age and medical history, and the overall administration schedule to be employed. Potential administration routes for relaxin include: parenteral, subcutaneous, intraperitoneal, intravenous, intramuscular, transdermal, transnasal, oral, transbronchial, topical.

A baseline dose for human patients is preferably determined for a given administration route by administering to a group of patients a control amount of relaxin equal to the normal level of relaxin in the human body during nonpregnant states (for women) and then further administering to other groups of patients increasing amounts of relaxin at two times, four times, and eight times, respectively, the control level of circulating relaxin to determine the dosage at which 90% of the patients report good pain relief. The level at which 90% of the patients report alleviation of pain and other symptoms of involuntary muscle dysfunction will be the baseline dose which can be modified as necessary for specific patient conditions.

It also may be desirable or necessary to couple administration of relaxin with estrogen and/or progesterone to achieve the desired synthesis and elevation of relaxin in the blood stream.

All references cited herein are expressly incorporated by reference.

Although the present invention has been described with reference to preferred embodiments, workers skilled in the art will recognize that changes may be made in form and detail without departing from the spirit and scope of the invention.

What is claimed is:

1. A method for remodelling collagen fibers, comprising applying topically to the epidermis of the skin a composition comprising effective amounts of relaxin hormone in an emollient vehicle in a program of maintenance therapy, whereby the skin substantially regains and maintains its firmness, turgor, and elasticity during said therapy, said composition and amounts of human relaxin hormone, being selected to provide a therapeutically effective dose of relaxin hormone.

2. The method of claim 1 wherein the skin is human facial skin.

3. The method of claim 1 wherein the skin is mammary gland skin.

* * * * *